US011596784B1

United States Patent
Zhen et al.

(10) Patent No.: US 11,596,784 B1
(45) Date of Patent: Mar. 7, 2023

(54) QUICK-CONNECTION TYPE MAGNETIC TRANSMISSION APPARATUS FOR USE IN MEDICAL INTERVENTIONAL INSTRUMENT

(71) Applicant: ForQaly Medical (Shanghai) Co., Ltd., Shanghai (CN)

(72) Inventors: Qiwen Zhen, Shanghai (CN); Dongliang Lu, Shanghai (CN); Bo Yu, Shanghai (CN)

(73) Assignee: FORQALY MEDICAL (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 17/789,021

(22) PCT Filed: May 9, 2020

(86) PCT No.: PCT/CN2020/089426
§ 371 (c)(1),
(2) Date: Jun. 24, 2022

(87) PCT Pub. No.: WO2021/128697
PCT Pub. Date: Jul. 1, 2021

(30) Foreign Application Priority Data

Dec. 24, 2019 (CN) .......................... 201911341482.6

(51) Int. Cl.
*A61M 25/18* (2006.01)
*A61B 5/273* (2021.01)
(Continued)

(52) U.S. Cl.
CPC .......... *A61M 60/414* (2021.01); *A61M 60/13* (2021.01); *A61M 60/216* (2021.01); *H01R 13/6205* (2013.01); *A61M 2205/0272* (2013.01)

(58) Field of Classification Search
CPC .......... A61M 2205/8287; A61M 60/00; A61M 60/13; A61M 60/148; A61M 60/237; A61M 60/414; A61M 60/419; A61M 60/85
See application file for complete search history.

(56) References Cited

U.S. PATENT DOCUMENTS

| | | | |
|---|---|---|---|
| 10,926,012 B2 | 2/2021 | Nusser et al. | |
| 2013/0096574 A1* | 4/2013 | Kang | A61B 17/16 606/130 |

FOREIGN PATENT DOCUMENTS

| | | |
|---|---|---|
| CN | 2326258 Y | 6/1999 |
| CN | 103893849 A | 7/2014 |
| (Continued) | | |

OTHER PUBLICATIONS

International Search Report and Written Opinion for International Application No. PCT/CN2020/089426, dated Sep. 28, 2020, 8 pages.

*Primary Examiner* — Jon Eric C Morales
(74) *Attorney, Agent, or Firm* — RatnerPrestia

(57) ABSTRACT

A quick-connection type magnetic transmission apparatus for use in a medical interventional instrument, comprising a drive-side housing and a driven-side housing. The drive-side housing and the driven-side housing are coaxially arranged and are connected in a nested mode; a magnetic coupling structure, a magnetic coupling and coaxial guiding mechanism, and an integral coaxial guiding mechanism are sequentially comprised from inside to outside; the magnetic coupling structure consists of a magnetic transmission drive end (12), a magnetic transmission driven end (11), and a quick-connection separation sleeve (13); the magnetic coupling and coaxial guiding mechanism consists of a magnetic coupling and guiding sleeve (21) and a magnetic coupling and guiding groove (22); the integral coaxial guiding mecha- (Continued)

nism consists of a coaxial guiding sleeve (31), a coaxial guiding groove (32), and a coaxial locking structure. The quick-connection type magnetic transmission apparatus for use in the medical interventional instrument uses a double guiding-locking fit structure, achieves quick connection, and ensures a minimal transmission gap.

10 Claims, 3 Drawing Sheets

(51) Int. Cl.
*A61M 39/10* (2006.01)
*A61M 60/414* (2021.01)
*A61M 60/13* (2021.01)
*H01R 13/62* (2006.01)
*A61M 60/216* (2021.01)

(56) References Cited

FOREIGN PATENT DOCUMENTS

| | | | |
|---|---|---|---|
| CN | 108025123 A | 5/2018 | |
| CN | 207907972 U | 9/2018 | |
| CN | 108880186 A | 11/2018 | |
| CN | 109921558 A | 6/2019 | |
| CN | 209285587 U | 8/2019 | |
| CN | 110743051 A | 2/2020 | |
| JP | 2016138542 A | 8/2016 | |
| WO | WO-2021128697 A1 * | 7/2021 | ............ A61M 60/00 |

* cited by examiner

QUICK-CONNECTION TYPE MAGNETIC TRANSMISSION APPARATUS FOR USE IN MEDICAL INTERVENTIONAL INSTRUMENT

CROSS-REFERENCE TO RELATED APPLICATIONS

This application is a 371 filing of International Application No. PCT/CN2020/089426, filed May 9, 2020, which claims priority to Chinese Application No. 201911341482.6, filed Dec. 24, 2019, the disclosure of these applications being incorporated herein by reference in their entireties for all purposes.

The present invention relates to a magnetic transmission apparatus and, more particularly, to a quick-connection type magnetic transmission apparatus for use in a medical interventional instrument.

BACKGROUND OF THE INVENTION

Magnetic transmission apparatus refers to a transmission technology in which a driving end drives a driven end to realize power transmission by using a coupling force generated by a magnetic material installed on the drive end and the driven end in a transmission component. The coupling forces include attractive and repulsive forces between the magnetic materials. For its non-contact power transmission, magnetic transmission is widely used. The magnetic transmission include main advantages that there is no rigid connection between transmission parts, overload protection can be provided, the structure is simple and easy to maintain, and dynamic seal can be converted into static seal, etc. The main applications include vacuum, spaceflight, medicine, food, scientific experiments, special chemical or high-risk fields. Due to the limitations of magnetic material technology, transmission torque stabilization should be a major limitation in various applications. At the same time, as the large-scale industrial environment, high torque, high stability, high life and maintenance are the main direction of improvement of magnetic transmission technology in recent years, there are a lot of structural improvements and inventions, especially for the distribution of magnetic material layout of the drive end and driven end.

For example, the invention patent document "a coaxial permanent magnet transmission apparatus" (CN 108880186A) proposes a new magnet coupling layout structure. Compared with the conventional coaxial magnetic transmission structure, this patent increases the magnetic torque that the magnetic transmission can provide by using the communication tube structure and increasing the magnet coupling pair.

For example, the utility model patent document "a magnetic transmission mechanism" (CN 207907972U) proposes an application of a magnetic transmission structure in the field of fuel gas sealing. By replacing the traditional seal structure with magnetic transmission, the static seal is transformed into the dynamic seal, which can reduce the transmission resistance and improve the structural stability.

In addition, the invention patent document "electromechanical magnetic transmission apparatus" (CN 109921558A) proposes a new layout structure of drive end and driven end. Compared with the traditional magnetic transmission structure, this patent achieves the purpose of improving the overall transmission efficiency of the system by adding a parallel mechanism so that one drive end can simultaneously drive multiple driven ends.

Compared with the traditional magnetic transmission structure, according to the key technical for the magnetic transmission of interventional devices, if in the clinical application, it requires more high rotation speed rather than high torque; and at the same time, the requirements for specification are higher relative to the transmission application. Accordingly, there remains a need for several aspects of improvements in torque transfer structures, such as a manually assisted blood pumping device, for use in an interventional blood pumping catheter device in which the power source is located outside the body.

1) It provides a smaller magnetic transmission structure specification, and can still maintain an effective magnetic transmission torque that can meet clinical applications while using miniature magnets; 2) fast connection structure and higher speed of magnetic transmission can meet the needs of high-speed rotation in the clinical application; and 3) effective magnet sealing ensures biocompatibility requirements for clinical use.

SUMMARY OF THE INVENTION

The technical problem to be solved by the present invention is to provide a quick-connection type magnetic transmission apparatus for use in a medical interventional instrument, which can meet the application requirements of a small-sized miniature magnetic transmission structure on the medical interventional instrument, and can achieve a high transmission rotation speed and a quick-connection operation.

The technical solution adopted in the present invention to solve the above-mentioned technical problem is to provide a quick-connection type magnetic transmission apparatus for use in a medical interventional instrument, comprising a drive-side housing and a driven-side housing, wherein the drive-side housing and the driven-side housing are coaxially arranged and are connected in a nested mode; a magnetic coupling structure, a magnetic coupling and coaxial guiding mechanism, and an integral coaxial guiding mechanism are sequentially comprised from inside to outside; the magnetic coupling structure consists of a magnetic transmission drive end, a magnetic transmission driven end and a quick-connection separation sleeve; the magnetic coupling and coaxial guiding mechanism consists of a magnetic coupling and guiding sleeve and a magnetic coupling and guiding groove; and the integral coaxial guiding mechanism consists of a coaxial guiding sleeve, a coaxial guiding groove and a coaxial locking structure; the magnetic transmission driven end comprises a driven rotor spacing sleeve; the coaxial guiding groove consists of an annular space between the inner wall of the driven-side outer shell and the outer wall of the driven-side inner shell; the magnetic coupling and guiding groove consists of a space between the inner wall of the driven-side inner shell and the outer wall of the driven rotor spacing sleeve; the inner wall surface of the driven-side inner shell is tightly fitted with the outer wall surface of the magnetic coupling and guiding sleeve; the magnetic transmission drive end is provided between the outer wall surface of the driven rotor spacing sleeve and the inner wall surface of the magnetic coupling and guiding sleeve; and the coaxial locking structure is a key groove provided on the drive-side housing and the driven-side housing and cooperating with each other.

According to the above-mentioned quick-connection type magnetic transmission apparatus for use in a medical interventional instrument, the magnetic transmission drive end consists of a driving rotor, a driving rotor spacing sleeve and a driving magnet; the driving rotor is a cylinder having a circular rotation space therein, and the inner surface of the cylinder is provided with a groove; and the driving rotor spacing sleeve is embedded in the circular rotating space, and forms a closed magnet placing groove together with the groove on the inner surface of the cylinder.

According to the above-mentioned quick-connection type magnetic transmission apparatus for use in a medical interventional instrument, the magnet placing grooves of the drive end have an even number of pairs, the magnets are placed in pairs in opposite directions, and the adjacent magnets have opposite polarities when unfolded in a circumferential direction.

According to the above-mentioned quick-connection type magnetic transmission apparatus for use in a medical interventional instrument, the magnetic transmission driven end further comprises a driven rotor, a driven magnet and a magnet holder, the driven rotor being a circular shaft; the magnet holder is an elongated cylinder, has a circular assembly space therein, and is assembled on the driven rotor; the driven rotor spacing sleeve is a cylinder and is assembled on the magnet holder; and the surface of the magnet holder is formed with a groove, and constitutes a magnet placing groove at the driven end together with the driven rotor and the driven rotor spacing sleeve.

According to the above-mentioned quick-connection type magnetic transmission apparatus for use in a medical interventional instrument, the magnet placing grooves of the driven end are an even number of pairs, the magnets are placed in pairs in an opposite direction, and adjacent magnets have opposite polarities when unfolded in a circumferential direction.

According to the above-mentioned quick-connection type magnetic transmission apparatus for use in a medical interventional instrument, the coaxial guiding sleeve and the coaxial guiding groove are fitted at a taper, the inner wall surface of the driven-side outer shell is tightly fitted with the outer wall surface of the coaxial guiding sleeve, and a gap is left between the outer wall surface of the driven-side inner shell and the inner wall surface of the coaxial guiding sleeve.

According to the above-mentioned quick-connection type magnetic transmission apparatus for use in a medical interventional instrument, the magnetic coupling and coaxial guiding mechanism and the integral coaxial guiding mechanism are fitted at the same taper, and the length of the integral coaxial guiding mechanism on the outside is greater than the length of the magnetic coupling and coaxial guiding mechanism on the inside.

According to the above-mentioned quick-connection type magnetic transmission apparatus for use in a medical interventional instrument, the taper between the coaxial guiding sleeve and the coaxial guiding groove is 6:100.

According to the above-mentioned quick-connection type magnetic transmission apparatus for use in a medical interventional instrument, a gap between the magnetic transmission drive end and the magnetic transmission driven end is 0.3-0.5 mm, and an overall outer diameter of the quick-connection type magnetic transmission apparatus is 3.5-4.0 cm.

According to the above-mentioned quick-connection type magnetic transmission apparatus for use in a medical interventional instrument, the quick-connection separation sleeve is located between the magnetic transmission drive end and the magnetic transmission driven end, the magnetic transmission driven end on the left side of the quick-connection separation sleeve is located on a catheter and belongs to a sterile area, and the magnetic transmission drive end on the right side is located on a power structure and belongs to a non-sterile area.

The present invention has the following advantageous effects compared to the prior art. A quick-connection type magnetic transmission apparatus for use in a medical interventional instrument provided by the present invention uses a double guide of a magnetic coupling and coaxial guiding mechanism and an integral coaxial guiding mechanism, which can ensure a high degree of coaxiality in a quick-connection operation, and meet the high-speed rotation requirements in clinical applications. The double guiding-locking fit structure can achieve fast connection while ensuring minimal transmission gap. The dynamic seal of the original transmission shaft is transformed into the static seal between the drive end and the driven end by the magnetic transmission. On the one hand, the seal wear is completely avoided and the transmission resistance is reduced. On the other hand, the driven end can be completely sealed, so as to ensure the sterility in the catheter in the clinical application.

Figure 1:
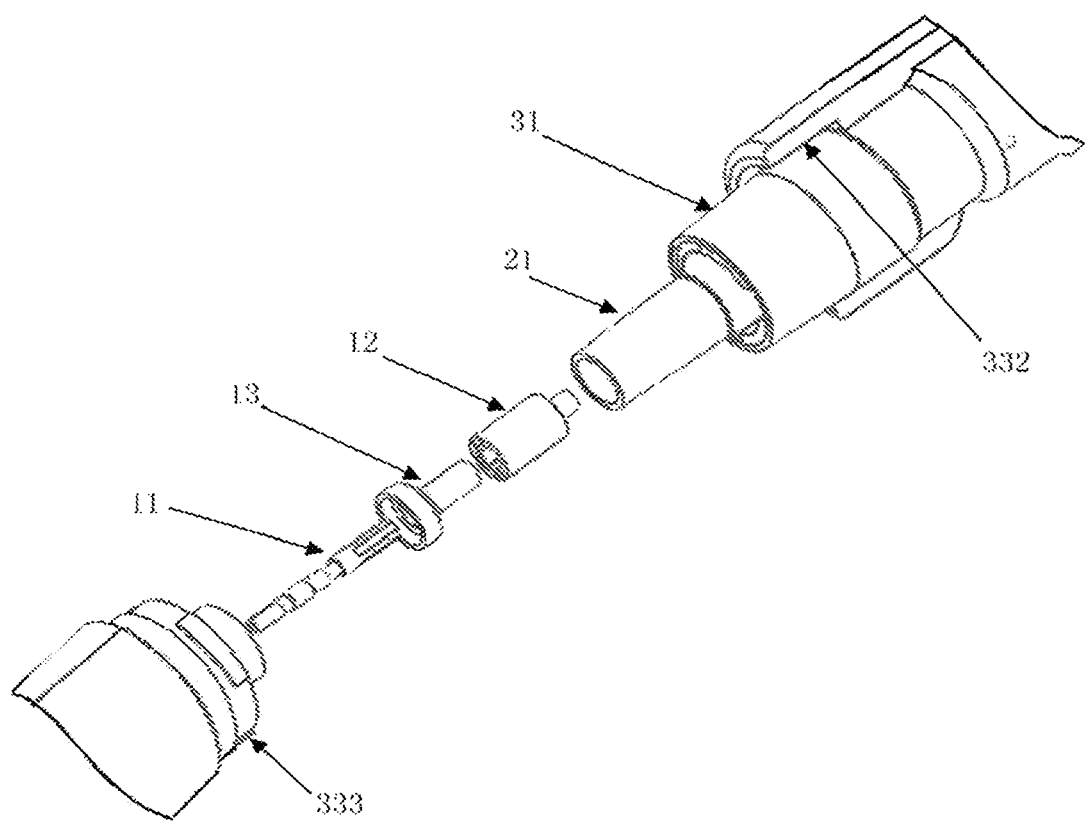
FIG. 1 is a schematic view of a quick-connection type magnetic transmission apparatus for use in a medical interventional instrument according to the present invention.

IN THE DRAWINGS 1 driven-side outer shell, 2 driven-side inner shell, 3 drive-side outer shell
11 magnetic transmission driven end, 12 magnetic transmission drive end, 13 quick-connection separation sleeve
21 magnetic coupling and guiding sleeve, 22 magnetic coupling and guiding groove, 31 coaxial guiding sleeve
32 coaxial guiding groove, 111 driven rotor
112 driven rotor spacing sleeve, 113 driven magnet, 114 magnet holder
121 driving rotor, 122 driving rotor spacing sleeve, 123 driving magnet
331 coaxial locking key, 332 coaxial locking groove, 333 locking ring

DETAILED DESCRIPTION OF THE INVENTION

The present invention are further described below in combination with the attached drawings and embodiments.

Figure 2:
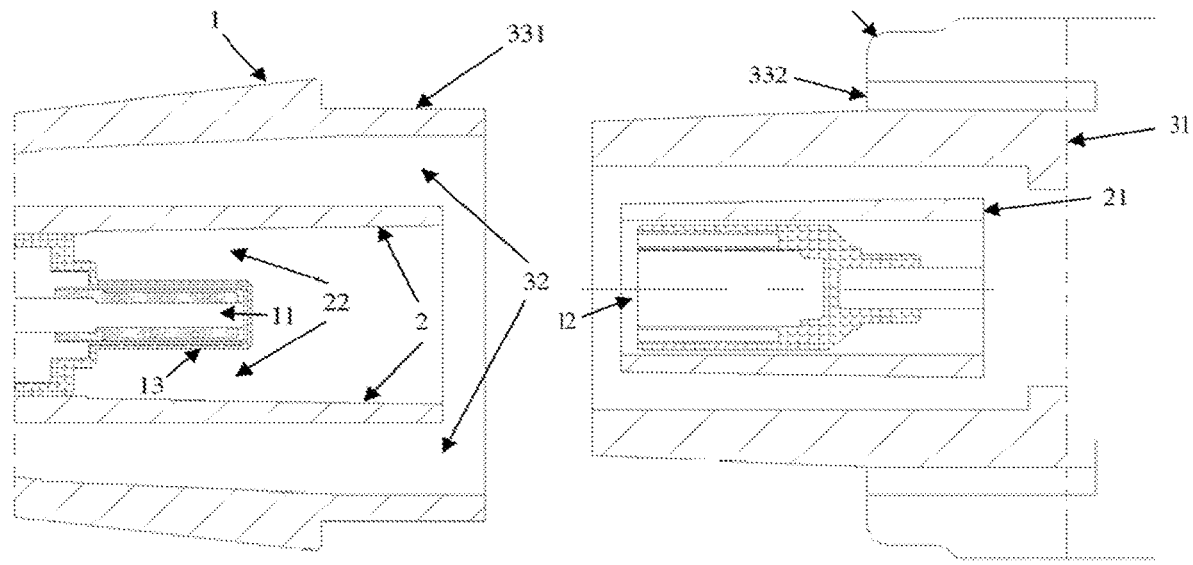
FIG. 2 is a sectional structure view of a quick-connection type magnetic transmission apparatus according to the present invention before connection.
Figure 3:
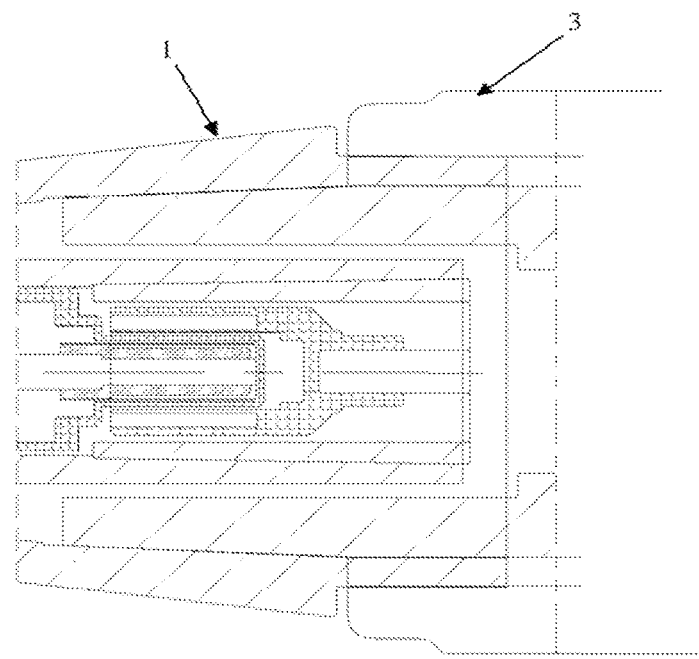
FIG. 3 is a sectional structure view of a quick-connection type magnetic transmission apparatus according to the present invention after connection.

Referring to FIGS. 1, 2 and 3, the present invention provides a quick-connection type magnetic transmission apparatus for use in a medical interventional instrument, comprising a drive-side housing and a driven-side housing, wherein the drive-side housing and the driven-side housing are coaxially arranged and are connected in a nested mode and are divided into three layers of a magnetic coupling structure, a magnetic coupling and coaxial guiding mechanism and an integral coaxial guiding mechanism according to functions from inside to outside. Herein, the magnetic coupling structure consists of a magnetic transmission drive end 12, a magnetic transmission driven end 11 and a quick-connection separation sleeve 13; the magnetic coupling and coaxial guiding mechanism consists of a magnetic coupling and guiding sleeve 21 and a magnetic coupling and guiding groove 22; and the integral coaxial guiding mechanism consists of a coaxial guiding sleeve 31, a coaxial guiding groove 32, and a coaxial locking structure. The magnetic transmission driven end 11 comprises a driven rotor spacing sleeve 112; the coaxial guiding groove 32 consists of an annular space between the inner wall of the driven-side outer shell 1 and the outer wall of the driven-side inner shell 2; the magnetic coupling and guiding groove 22 consists of a space between the inner wall of the driven-side inner shell 2 and the outer wall of the driven rotor spacing sleeve 112; the inner wall surface of the driven-side inner shell 2 is tightly fitted with the outer wall surface of the magnetic coupling and guiding sleeve 21; and the magnetic transmission drive end 12 is provided between the outer wall surface of the driven rotor spacing sleeve 112 and the inner wall surface of the magnetic coupling and guiding sleeve 21.

The core difficulty of quick connection and achieving high-speed rotational stability lies in ensuring the coaxiality of the abutment. In addition, the outer diameter of the quick-connection type magnetic transmission structure of the present invention is significantly reduced relative to the transmission structure, and the reduction of the outer diameter correspondingly results in the decrease of the connection strength, requiring a longer axial mating distance to compensate, thus further increasing the coaxiality difficulty. For this reason, the present invention provides a quick-connection type magnetic transmission apparatus using a double guiding-locking fit structure to provide sufficient connection strength to ensure the coaxiality. After the quick connect is inserted into place, a tight fit is formed between the guide sleeve and the guide groove.

The coaxial locking structure is a key groove provided on the drive-side housing and the driven-side housing and cooperating with each other. For example, a coaxial locking key 331 is formed at one end of the driven-side housing 1, and a coaxial locking groove 332 is provided at one end of the drive-side housing 3. Before insertion, the coaxial locking groove 332 is in the "on" position. After the coaxial locking key 331 is inserted into place, the coaxial locking groove 332 is adjusted to the "off" position to complete locking. In addition, a locking ring 333 may be further provided on the driven-side housing 1.

Figure 4:
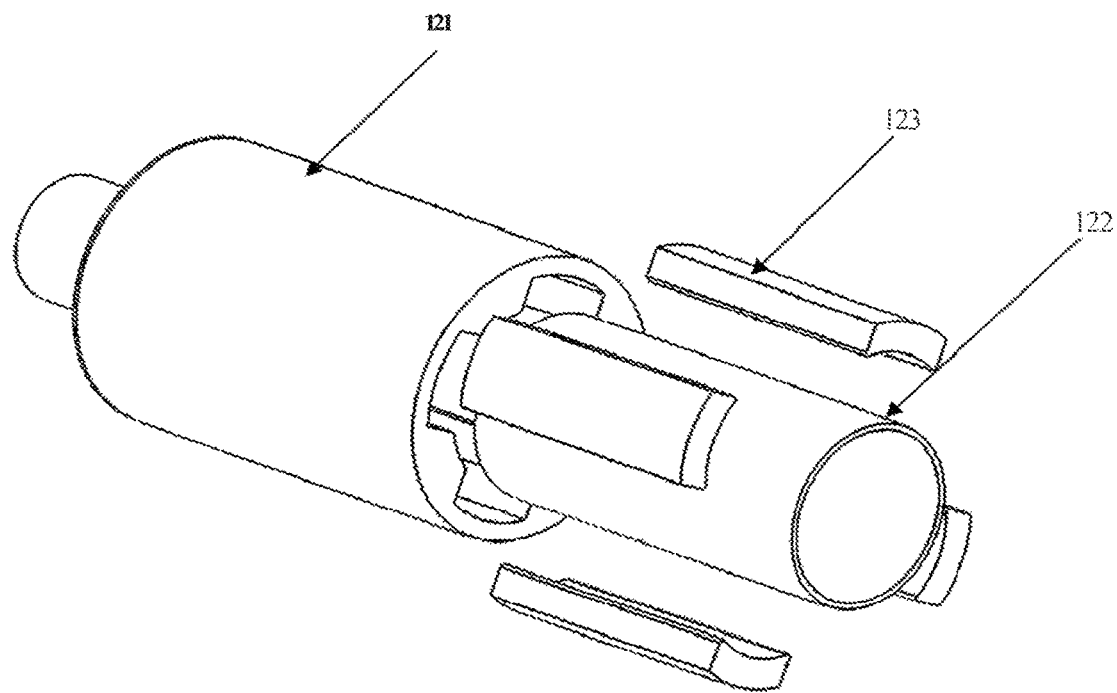
FIG. 4 is an exploded view showing the structure of a magnetic transmission drive end of a quick-connection type magnetic transmission apparatus according to the present invention.

With continued reference to FIG. 4, the magnetic transmission drive end 12 is comprised of a driving rotor 121, a driving rotor spacing sleeve 122, and a driving magnet 123. Herein, the driving rotor 121 is a cylinder having a circular rotation space therein, and the inner surface of the cylinder is provided with a groove; the driving rotor spacing sleeve 122 is embedded in the circular rotating space, and forms a closed magnet placement groove together with the groove on the inner surface. The magnet placement grooves at the drive end shall be an even number of pairs. When the magnets are placed, they shall be placed in pairs in opposite directions. When the magnets are unfolded in the circumferential direction, the adjacent magnets have opposite polarities. The driving rotor spacing sleeve 122 and the driving rotor 121 are performed with integral injection moulding during processing to achieve assembly, so as to constitute a magnet accommodating cavity. After the driving magnet 123 is placed in the magnet receiving cavity, the adhesive port is closed with the medical grade glue. The other end of the magnetic transmission drive end 12 is tightly connected to a driving motor, and the driving motor is fixed in the drive-side housing via a buffering structure. The above-mentioned assembly relationship is a conventional assembly structure, and will not be described in detail herein.

Figure 5:
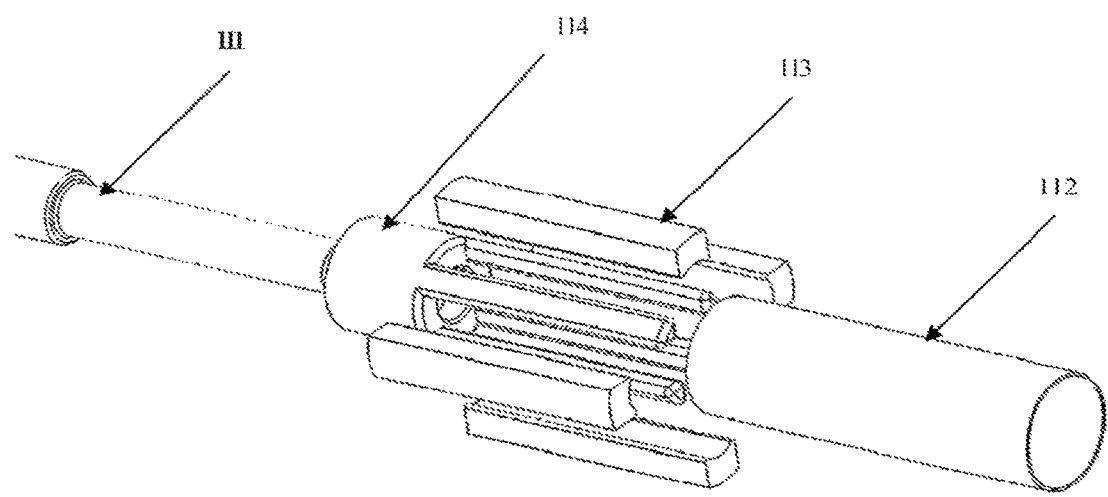
FIG. 5 is an exploded view showing the structure of a magnetic transmission driven end of a quick-connection type magnetic transmission apparatus according to the present invention.

With continued reference to FIG. 5, the magnetic transmission driven end 11 is comprised of a driven rotor 111, a driven rotor spacing sleeve 112, a driven magnet 113, and a magnet holder 114. Herein, the driven rotor 111 is a circular shaft, and the magnet holder 114 is an elongated cylinder, has a circular assembly space therein, and is assembled on the driven rotor 111; the driven rotor spacing sleeve 112 is a cylinder and is assembled on the magnet holder 114; the magnet holder 114 has a groove on its surface, and constitutes a magnet placing groove at the driven end together with the driven rotor 111 and the driven rotor spacing sleeve 112. The magnet placing grooves on the driven end shall be an even number of pairs. When the magnets are placed, they shall be placed in pairs in opposite directions. When the magnets are unfolded in the circumferential direction, the adjacent magnets have opposite polarities. The other side of the magnetic transmission driven end 11 is fitted with a support bearing (not shown), the support bearing is tightly fitted inside the driven-side inner shell 2, and the driven-side inner shell 2 is fixed inside the driven-side outer shell 1 via the buffering structure. The above assembly is also a conventional assembly structure and will not be described in detail herein.

In the magnetic coupling structure of the present invention, the magnetic transmission driven end 11 and the magnetic transmission drive end 12 are separated by a quick-connection separation sleeve 13. When the transmission structure is applied to the interventional catheter, the magnetic transmission driven end 11 on the left side of the quick-connection separation sleeve 13 is located on a catheter and belongs to a sterile area, and the magnetic transmission drive end 12 on the right side is located on a power structure and belongs to a non-sterile area.

The magnetic coupling and coaxial guiding mechanism of the present invention cooperates with the integral coaxial guiding mechanism to restrict a small rotation gap between the drive end and the driven end at the inner and outer sides of the quick-connection separation sleeve 13, so as to ensure the coaxiality of the both ends after the quick-connection insertion and withdrawal, thereby achieving the requirements of high rotation speed and stability. Since the gap between the magnetic transmission drive end 12 and the magnetic transmission driven end 11 is only 0.3-0.5 mm, the wall thickness of the quick-connection separation sleeve 13 is about 0.3 mm in a magnetic transmission mating area. The bottom of the quick-connection separation sleeve 13 is assembled and placed with the bottom of the magnetic coupling and coaxial guiding mechanism. In order to ensure the strength and coaxiality of the assembly part, the wall thickness of the quick-connection separation sleeve 13 is thickened to 1.0 mm at the assembly position.

In order to achieve a shorter axial mating distance and obtain a greater connection strength, the coaxial guiding sleeve 31 and the coaxial guiding groove 32 of the present invention are further provided with a 6% mating taper to achieve insertion guidance while improving the mating strength after insertion into place. There is an offset in the axial direction of the two guide mating structures. When it is inserted quickly, the outer integrated coaxial guide mating structure firstly contacts to perform integrated coarse guide control, and the inner magnetic coupling coaxial guide mating structure continues to be inserted to start contacting to perform precise guide control of the magnetic coupling structure. Furthermore, the two guide mating structures have a length difference while adopting the same taper. Compared with the magnetic coupling and coaxial guiding mechanism, the length of the integrated coaxial guide mechanism located outside is longer. During the insertion operation, the insertion resistance increases nonlinearly due to the axial offset of the inner and outer structures. The insertion resistance is lower before the magnetic coupling coaxial guide contacts. After the magnetic coupling coaxial guide contacts, the insertion resistance increases rapidly, which can ensure the final mating strength and avoid the high difficulty of fast insertion.

Compared with the magnetic transmission structures in the conventional industry, the present invention is applicable to micro-structures, high rotational speed, and low torque type applications in medical interventional devices. With the magnetic transmission architecture of the present invention, a quick-connection operation is achieved while the overall outer diameter of the structure can be controlled to within 4.0 cm and stable operation of the structure can be ensured at a maximum magnetic transmission speed of 50000 RPM.

The present invention firstly converts the dynamic seal of the original transmission shaft into a static seal between the drive end and the driven end by a magnetic transmission. On the one hand, the seal wear is completely avoided and the transmission resistance is reduced. On the other hand, the driven end can be completely sealed so as to ensure the sterility in the catheter after sterilization in clinical application.

Further, the present invention uses a double guiding-locking fit structure, achieves quick connection, and ensures a minimal transmission gap. On the one hand, under the condition that the medical catheter is used as a consumable for a single time but the high-value power structure is expected to be used for multiple times, one power drive end can be used with different driven ends for multiple times, which saves the cost of use and improves the reliability of the system because the power structure does not need to be sterilized again. On the other hand, the guide structure stably controls the rotational gap between the driving and driven ends within a very small gap of 0.5 mm, providing sufficient torque in a small size structure by achieving a smaller controlled magnetic drive gap.

Although the present invention has been described with reference to the preferred embodiments, it is restricted by the embodiments. Those skilled in the art may make some modifications and improvements without departing from the spirit and scope of the invention. Therefore, the scope of the present invention should be determined by the appended claims.

The invention claimed is:

1. A quick-connection type magnetic transmission apparatus, comprising a drive-side housing and a driven-side housing, the driven-side housing including a driven-side outer shell and a driven-side inner shell, wherein the drive-side housing and the driven-side housing are coaxially arranged and are connected in a nested mode; a magnetic coupling structure, a magnetic coupling and coaxial guiding mechanism, and an integral coaxial guiding mechanism are sequentially comprised from inside to outside; the magnetic coupling structure consists of a magnetic transmission drive end, a magnetic transmission driven end and a quick-connection separation sleeve; the magnetic coupling and coaxial guiding mechanism consists of a magnetic coupling and guiding sleeve and a magnetic coupling and guiding groove; and the integral coaxial guiding mechanism consists of a coaxial guiding sleeve, a coaxial guiding groove and a coaxial locking structure;

the magnetic transmission driven end comprises a driven rotor spacing sleeve; the coaxial guiding groove consists of an annular space between the inner wall of the driven-side outer shell and the outer wall of the driven-side inner shell; the magnetic coupling and guiding groove consists of a space between the inner wall of the driven-side inner shell and the outer wall of the driven rotor spacing sleeve; the inner wall surface of the driven-side inner shell is tightly fitted with the outer wall surface of the magnetic coupling and guiding sleeve; and the magnetic transmission drive end is provided between the outer wall surface of the driven rotor spacing sleeve and the inner wall surface of the magnetic coupling and guiding sleeve;

the coaxial locking structure is a key groove provided on the drive-side housing and the driven-side housing and cooperating with each other.

2. The quick-connection type magnetic transmission apparatus according to claim 1, wherein the magnetic transmission drive end consists of a driving rotor, a driving rotor spacing sleeve and a driving magnet; the driving rotor is a cylinder having a circular rotation space therein, and the inner surface of the cylinder is provided with a groove; and the driving rotor spacing sleeve is embedded in the circular rotating space, and forms a closed magnet placing groove together with the groove on the inner surface of the cylinder.

3. The quick-connection type magnetic transmission apparatus according to claim 2, wherein the magnet placing grooves of the magnetic transmission drive end have an even number of pairs, the magnets are placed in pairs in opposite directions, and the adjacent magnets have opposite polarities when unfolded in a circumferential direction.

4. The quick-connection type magnetic transmission apparatus according to claim 1, wherein the magnetic transmission driven end further comprises a driven rotor, a driven magnet and a magnet holder, the driven rotor being a circular shaft; the magnet holder is an elongated cylinder, has a circular assembly space therein, and is assembled on the driven rotor; the driven rotor spacing sleeve is a cylinder and is assembled on the magnet holder; and the surface of the magnet holder is formed with a groove, and constitutes a magnet placing groove at the driven end together with the driven rotor and the driven rotor spacing sleeve.

5. The quick-connection type magnetic transmission apparatus according to claim 4, wherein the magnet placing grooves of the driven end are an even number of pairs, the magnets are placed in pairs in an opposite direction, and adjacent magnets have opposite polarities when unfolded in a circumferential direction.

6. The quick-connection type magnetic transmission apparatus according to claim 1, wherein the coaxial guiding sleeve and the coaxial guiding groove are fitted at a taper, the inner wall surface of the driven-side outer shell is tightly fitted with the outer wall surface of the coaxial guiding sleeve, and a gap is left between the outer wall surface of the driven-side inner shell and the inner wall surface of the coaxial guiding sleeve.

7. The quick-connection type magnetic transmission apparatus according to claim 6, wherein the magnetic coupling and coaxial guiding mechanism and the integral coaxial guiding mechanism are fitted at the same taper, and the length of the integral coaxial guiding mechanism on the outside is greater than the length of the magnetic coupling and coaxial guiding mechanism on the inside.

8. The quick-connection type magnetic transmission apparatus according to claim 6, wherein the taper between the coaxial guiding sleeve and the coaxial guiding groove is 6:100.

9. The quick-connection type magnetic transmission apparatus according to claim 1, wherein a gap between the magnetic transmission drive end and the magnetic transmission driven end is 0.3-0.5 mm, and an overall outer diameter of the quick-connection type magnetic transmission apparatus is 3.5-4.0 cm.

10. The quick-connection type magnetic transmission apparatus according to claim 1, wherein the quick-connection separation sleeve is located between the magnetic transmission drive end and the magnetic transmission driven end, the magnetic transmission driven end on the left side of the-connection separation sleeve is located on a catheter and belongs to a sterile area, and the magnetic transmission drive end on the right side is located on a power structure and belongs to a non-sterile area.

* * * * *